United States Patent [19]

Berniere et al.

[11] 4,012,870
[45] Mar. 22, 1977

[54] APPARATUS FOR MEASURING AND CHANGING VIBRATION FREQUENCY OF METAL B

[76] Inventors: Michel G. Berniere, 4 Allee des Hauts-Dimanches, 78430 Louveciennes; Didier M. Beaudet, 86 rue Elias Howe, 94100 Saint-Maur des Fosses, both of France

[22] Filed: June 25, 1975

[21] Appl. No.: 590,034

[30] Foreign Application Priority Data

July 3, 1974 France .............................. 74.23143
Apr. 4, 1975 France .............................. 75.10602

[52] U.S. Cl. ........................ 51/165 R; 51/165.74; 73/67
[51] Int. Cl.² ....................................... B24B 49/10
[58] Field of Search ............ 73/67, 67.2; 51/217 R, 51/165 R, 165.91, 165.74

[56] References Cited

UNITED STATES PATENTS

| | | | |
|---|---|---|---|
| 2,320,390 | 6/1943 | Shmurak | 73/67.2 X |
| 2,340,843 | 2/1944 | Bailey | 51/165 R |
| 2,782,633 | 2/1957 | Stauss | 73/67.2 |
| 3,095,532 | 6/1963 | Floyd | 73/67 X |
| 3,121,955 | 2/1964 | King | 73/67 |
| 3,250,119 | 5/1966 | Roberts | 73/67.2 |
| 3,345,862 | 10/1967 | Rowe | 73/67.2 |
| 3,488,674 | 1/1970 | Simjian | 51/217 R |
| 3,580,056 | 5/1971 | Warner | 73/67.2 |

*Primary Examiner*—Harold D. Whitehead
*Attorney, Agent, or Firm*—Flynn & Frishauf

[57] ABSTRACT

A method of measuring and, where necessary, modifying the natural vibration frequency of a metal bar, more especially a ferromagnetic bar, comprising freely suspending the bar in a constant magnetic field, subjecting the bar to action from outside to make it vibrate and detecting the resulting vibration frequency. There is also provided apparatus for carrying out the method, which comprises a vertical insulating cylinder, at the center of which the bar is kept freely suspended by a pneumatic device, means intended to make the bar vibrate, a solenoid which establishes a constant magnetic field and at the terminals of which the vibration frequency of the bar is detected, and a selective amplifier connected to the terminals of the solenoid.

14 Claims, 3 Drawing Figures

APPARATUS FOR MEASURING AND CHANGING VIBRATION FREQUENCY OF METAL B

FIELD OF THE INVENTION

This invention relates to a method of and an apparatus for measuring and, where necessary, adjusting the vibration frequency of a metal bar, more especially a ferromagnetic bar.

PRIOR ART

Mechanically vibrating bars of this kind are used in particular in oscillators or electromechanical frequency filters.

It is known that a free ferromagnetic bar has clearly defined mechanical vibration frequencies which form an infinite series of discrete values $f_1, f_2 \ldots f_n$. The value $n = 1$ represents the fundamental vibration, and the bar will vibrate in half waves, whilst the value $n = 2$ represents the second harmonic and the bar will vibrate in whole waves, and so on for any value of $n$. The vibration frequency of the bar is governed by its geometric parameters and, in particular, by its length when its diameter is small in relation to its length. More precisely, the vibration frequency is inversely proportional to the length of the bar.

The vibration frequency is normally measured by using the phenomenon of magnetostriction and, more precisely, the direct effect known as the longitudinal Joule effect, according to which any application of a magnetic field or variation of the field applied to a ferromagnetic bar produces a variation in length, i.e. a longitudinal pressure wave. This effect is used in particular for generating sounds or ultra-sounds.

The bar whose vibration frequency it is desired to measure is subjected to a magnetic field modulated with a variable frequency $f$. Under the Joule effect, the bar begins to vibrate longitudinally at the frequency $f$. When this frequency $f$ tends to coincide with one of the natural vibration frequencies of the bar, a resonance phenomenon is observed and the amplitude of vibration of the bar assumes values much higher (by 100 to 1000 times) than those due to the Joule effect. The value $f$ of the alternating field is thus superimposed upon the value of the measured frequency.

If it is desired to obtain a desired vibration frequency, the corresponding length of the bar is calculated, a blank of approximate dimensions is prepared and its length modified by successive aftertreatments, the vibration frequency of the bar being measured after each operation.

Accordingly, this process of adjusting the length of a bar is time-consuming, tedious and delicate on account of the difficulties encountered in accurately detecting the resonance phenomenon.

OBJECT OF THE INVENTION

The object of the present invention is to obviate these disadvantages by providing a simple apparatus for measuring the frequency of a metal bar and, where necessary, adjusting its length to obtain a desired vibration frequency.

BRIEF SUMMARY OF THE INVENTION

The invention is also based on the phenomenon of magnetostriction, but uses the opposite effect to the longitudinal Joule effect, namely the Villari effect, according to which the creation of a pressure wave or a variation in the natural length of a ferromagnetic bar results in the magnetisation of that bar.

This effect is used in particular for receiving and detecting ultra-sounds. In this case, the bar is placed in a solenoid. The pressure wave accompanying the ultrasonic wave applies an alternating force of which the amplitude is equal to that of the pressure wave.

In response to the resulting variation in length, the bar acquires an alternating magnetisation which induces an alternating voltage of the same frequency in the solenoid surrounding the bar.

The method according to the invention uses this effect in a different way; it comprises freely suspending the ferromagnetic bar in a constant magnetic field, subjecting this bar to action from outside to make it vibrate and detecting the resulting vibration frequency.

In cases where it is merely desired to measure the vibration frequency, for example in order to classify bars according to narrow frequency bands, vibration of the bar may be obtained, for example, by mechanical means such as a hammer striking the upper end of the freely suspended bar.

FURTHER FEATURES OF THE INVENTION

In another embodiment, vibration of the bar is obtained by electrical excitation, more especially by an electrical shock.

In cases where it is desired simultaneously to adjust the length of the bar whose frequency is measured in order to obtain a desired vibration frequency, vibration of the bar is obtained by the action of a machining tool on one end of the bar, the resulting vibration frequency being compared with the desired frequency and the action of the tool being automatically terminated when these two values become equal.

The apparatus for carrying out the method according to the invention essentially comprises a vertical insulating cylinder at the centre of which the bar is freely suspended by means of a pneumatic device, means intended to vibrate the bar, a solenoid which establishes a constant magnetic field and at the terminals of which the vibration frequency of the bar is detected, and a selective amplifier connected to the terminals of the solenoid.

In cases where it is merely desired to measure frequency, the apparatus according to the invention comprises a frequency-measuring stage connected to the output of the selective amplifier.

In cases where it is simultaneously desired to adjust the length of the bar in order to obtain a desired frequency, the apparatus additionally comprises a comparator whose output signal controls the pneumatic device in such a way that it controls the interaction of the tool and the end of the bar. This pneumatic device applies to the bar a force with a first high value, keeping said bar in an upper position in which it comes into contact with the tool when the output signal of the comparator indicates that the desired frequency has not been reached, and a second low value keeping the bar in a lower position in which it is separated from the tool when the comparator indicates that the desired frequency has been obtained.

In one preferred embodiment of the invention, the pneumatic device comprises a compressed air source of constant and adjustable output and pressure, and a distribution block connected to the lower part of the insulating cylinder accommodating the bar through a connecting element with an inner, preferably circular, cavity into which directly open the lower end of the insulating cylinder and the upper end of a central air-inlet nozzle, which is situated in the extension of the insulating cylinder and which may be connected to the compressed air source, and at least one lateral outlet nozzle defining the equilibrium position of the bar.

DESCRIPTION OF EMBODIMENTS

Several particular embodiments of the invention are described by way of example in the following with reference to the accompanying drawings, wherein.

In the Figures, identical components are denoted by the same reference numerals.

Figure 1:
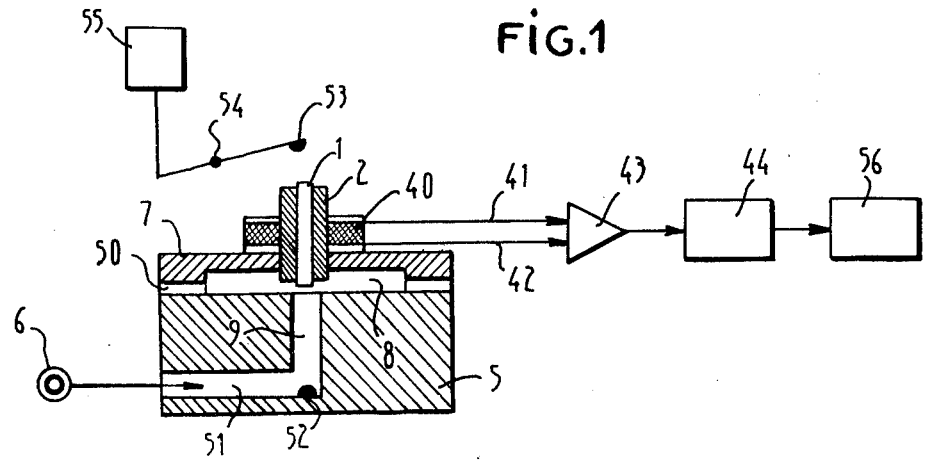
FIG. 1 is a basic diagram, partly in section, of a first embodiment of an apparatus according to the invention for measuring the frequency of a metal bar.

As can be seen from the Figures, more especially from FIG. 1, the bar 1 whose frequency is to be measured is arranged in a vertical insulating cylinder 2 inside which it is able to slide without friction.

The force by which the bar 1 is suspended is supplied by a pneumatic device essentially comprising a compressed air source 6, of which the output and pressure are constant and may be adjusted to any desired value, and a distribution block 5 communicating, on the one hand, with the compressed air source 6 and, on the other hand, with an exhaust system opening into the atmosphere. The distribution block 5 is connected to the lower part of the insulating cylinder 2 through a connecting element 7 formed with a circular cavity 8 into which open the lower end of the insulating cylinder 2 and the upper end of a central nozzle 9 and one end of at least one lateral nozzle 50 whose other end opens into the atmosphere. The central nozzle 9, formed in the distribution block 5, is vertical and aligned with the centre of the insulating cylinder 2 and, as a result, is situated directly below the bar 1.

In this first embodiment, the means intended to vibrate the bar 1 are in the form of a hammer 53 which pivots about a fixed axis 54 and which is actuated by any suitable means 55, for example an electromagnet comprising a plunger core connected to the rear end of the hammer.

The percussion effect of the hammer 53 on the top of the bar 1 causes the bar to vibrate and to descend into the vertical nozzle 9. In view of the thrust applied by the compressed air coming from the source 6, the speed of the bar drops to zero in the lower part of the tube and the bar ascends back towards its equilibrium position.

The central nozzle 9 is bent at right angles and is extended by a horizontal bore 51 connected to the compressed air source 6. The base of the central nozzle, situated at the bend, is provided with an elastic stop 52 against which the bar may rebound when it is in motion.

The nozzles 9 and 10 are used respectively for the admission and exhaust of the compressed air coming from the source 6. The horizontal nozzles 50 are formed in the connecting element 7 and their position determines the equilibrium position of the bar 1 in the insulating cylinder 2. Their number and/or dimensions are sufficiently large to allow free exhaust without any obstacles.

A solenoid 40 arranged around the insulating cylinder 2, of which the feed has not been shown, establishes a constant magnetic field around the bar 1. This constant magnetic field has superimposed on it the alternating magnetic field created by the vibration of the bar when it is struck by the hammer. The output terminals 41, 42 of the solenoid 40 are connected to the inputs of an amplifier 43 of which the very narrow bandwidth is centred on a frequency of the other of that of the bars whose vibration frequency it is desired to measure. This amplifier 43 is followed by a band-pass filter 44. The output signal of the filter 44 is applied to a device 56 for measuring the frequency.

In the embodiment illustrated, the device 56 is in the form of a frequencymeter which measures the frequency of the voltage induced at the terminals 41 and 42 of the solenoid which is applied to it through the amplifier 43 and the filter 44 each time the bar is made to vibrate and is situated at the level of the solenoid 40, i.e. placed in a constant magnetic field either during the descent of the bar or during its re-ascent, optionally after having rebounded against the elastic stop.

In one variant (not shown) of this embodiment, given the fact that the bar 1 descends into the central nozzle and, hence, leaves the constant magnetic field, the frequencymeter may be replaced by a chronometer which measures the time required to count a predetermined number of passages through zero of the signal at the terminals of the solenoid when the bar traverses it, which gives a measure of the frequency.

Figure 2:
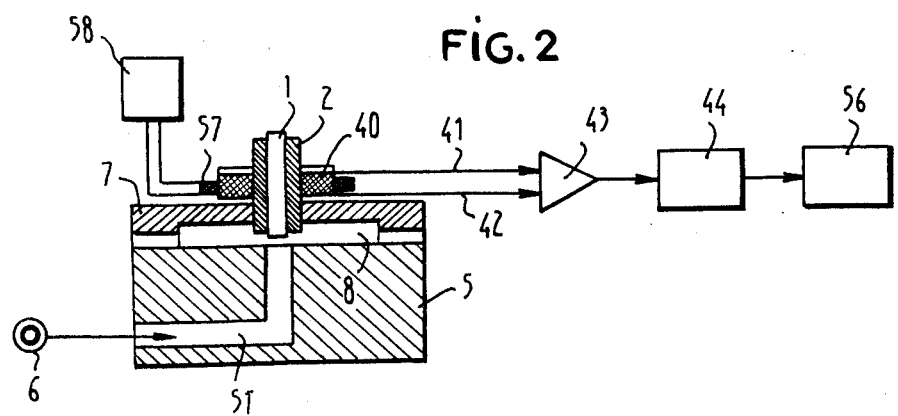
FIG. 2 shows a variant of the apparatus shown in FIG. 1.

FIG. 2 illustrates a second embodiment in which the external effect causing the bar to vibrate is an electrical shock. To this end, a second solenoid or auxiliary solenoid 57 is arranged around the first solenoid 40. This auxiliary solenoid is fed by an impulse generator 58. The other elements and circuits are identical with those of the first embodiment and are denoted by the same reference numerals, their operation also being identical.

In this embodiment, vibration of the bar 1 is obtained by the application to the auxiliary solenoid 57 of a high-intensity short-duration impulse delivered by the impulse generator 58 of known type. The resulting electrical shock causes the bar to vibrate without making it leave the insulating cylinder, so that no stop is necessary at the base of the nozzle 9. The frequency of the voltage appearing at the terminals of the solenoid 40 is detected by the frequencymeter 56 after amplification and filtration by the amplifier 43 and the filter 44, respectively.

In one variant, electrical excitation of the bar may be obtained by applying to the auxiliary solenoid 57 a current of variable frequency rather than a brief high-intensity impulse. In another variant, the auxiliary solenoid may even by omitted and the bar made to vibrate by superimposing a voltage of variable frequency on the feed of the first solenoid 40.

Figure 3:
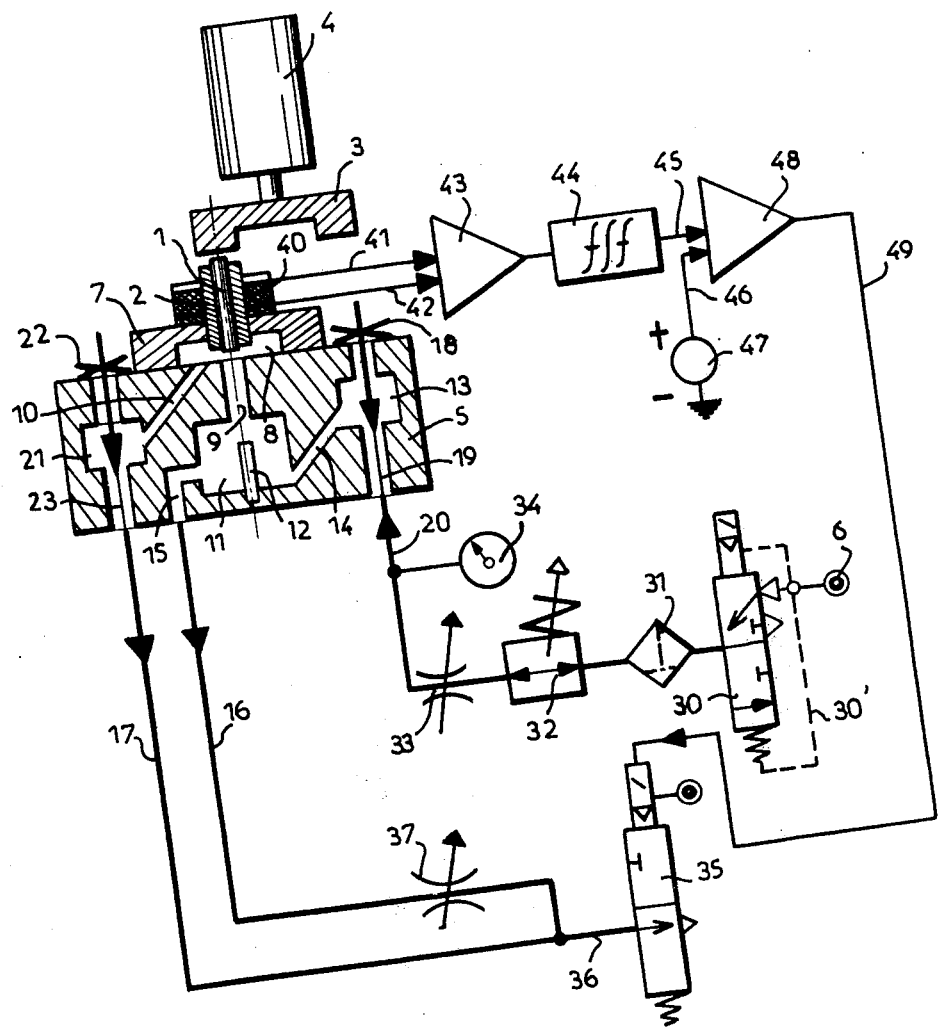
FIG. 3 is a basic diagram, partly in section, of an apparatus according to the invention for measuring and adjusting the frequency of a metal bar.

FIG. 3 shows an improved embodiment by which it is possible not only to measure the vibration frequency of a metal bar, but also to adjust the length of that bar to obtain a desired frequency.

As in FIGS. 1 and 2, the bar 1 whose length may have to be adjusted is arranged in a vertical insulating cylinder 2 inside which it is able to slide without friction. Above the cylinder 2 there is a tool 3 used for modifying the length of the bar. In this case, the tool 3 is in the form of a grinding wheel 3 mounted on the output shaft of a motor 4 rotating at constant speed. In a variant, the grinding wheel may be replaced by a smooth surface.

The frequency detection system, consisting of the solenoid 40, the amplifier 43 and the selective filter 44, is identical with that shown in FIGS. 1 and 2.

By contrast, the output signal of the filter 44 in this case is applied to an input 45 of a comparator 48 of which the other input 46 receives a reference signal supplied by a reference source 47. The output signal of the comparator 48, appearing on the conductor 49, is used for controlling the pneumatic device by which the bar is freely suspended so that it controls the interaction between the tool 3 and the upper end of the bar 1.

This pneumatic device essentially comprises a compressed air source 6 of constant and adjustable output and pressure, and a distribution block 5 connected to the lower part of the insulating cylinder 2 through a connecting element 7 formed with an inner, preferably circular cavity 8 into which directly open the lower end of the insulating cylinder 2 and the upper end of a central nozzle 9 and a lateral nozzle 10. The central nozzle 9 opens into the extension of the insulating cylinder and may be connected to the compressed air source by means which will be described hereinafter.

The lateral nozzle 10 is laterally inclined and opens onto the upper surface of the block 5 on one side of the central nozzle 9. The central and lateral nozzles 9 and 10 are used respectively for the admission and exhaust of the compressed air coming from the source 6. The lower end of the central nozzle 9 opens into a central cavity 11 at the base of which is arranged a support 12 which prevents the bar from falling transversely by keeping its upper end engaged in the central nozzle when the bar is in its lower position. This central cavity 11 communicates, on the one hand, with a first lateral cavity 13 through the bore 14 and, on the other hand, with a bore 15 which itself is connected to a first exhaust bore 16 comprising an output regulator 37. The lateral cavity 13 contains a flow-regulating device 18 which, in the present case, is in the form of a pointed screw, and communicates through a bore 19 with a bore 20 for the introduction of compressed air.

At its lower end, the lateral nozzle 10 communicates with a second lateral cavity 21 containing a flow-regulating means 22 in the form of a point screw which communicates with a bore 23 which itself is connected to a second exhaust bore 17.

Compressed air is admitted from the high-pressure source 6 through a normally open electrovalve 30, to the output of which a filter 31 is connected. The apparatus as a whole is started and stopped through the connection 30', shown is dotted lines, which is connected in series with a start-stop button.

The filter 31 is connected to a pressure regulator 32 which itself is followed by a flow regulator 33. The pressure prevailing in the inlet bore 20 is controlled by a manometer 34. Exhaust takes place through a second, normally closed electrovalve 35 which is selectively controlled, as will be seen hereinafter, and to which leads an exhaust bore 36 formed by the joining of the exhaust bores 16 and 17.

The apparatus additionally comprises means for introducing the bar, at its original natural length, and for discharging the bar at its final length, which do not form any part of the invention and, for this reason, will not be described.

The apparatus described above operates as follows:

The bar 1 in the insulating tube 2 is subjected at its lower end to a constant compressive force which is necessary and sufficient for keeping it in contact with the abrasive surface.

The intensity of this force, which is due to the air under pressure admitted into the central cavity 11 and which is applied to the lower end of the bar through the central nozzle 9, is regulated by means of different regulating devices 32, 33 for the intake bore 20 and the point screw 18.

At the upper end of the bar, each abrasive grain of the grinding wheel, while the bar is in contact with the grinding wheel, applies a pressure which may be assumed to be constant. However, the composition of all these individual forces gives a resulting, arbitrary force which varies according to the composition of the bar.

Under the effect of this arbitrary force, the bar vibrates at any of the multiples or submultiples of the natural frequency of the bar for which a vibration node appears at the aforementioned end of the bar. The vibration frequency varies at the same time as the length of the bar and in an inversely proportional manner.

The mechanical vibration of the bar causes an alternating magnetisation of the bar which induces an alternating voltage of the same frequency at the terminals of the solenoid 40 arranged around the insulating cylinder 2.

When this frequency, which increases as the length of the bar decreases, reaches the lower threshold value of the amplifier 43, the amplifier supplies an output signal which is transmitted to the band-pass filter 44 and is then applied to the input 45 of the comparator 48. On the other hand, the comparator 48 receives, at its terminal 46, a reference signal corresponding to the desired vibration frequency. As long as the vibration frequency remains below the desired value, the signal applied to the terminal 45 remains below the threshold value predetermined by the reference source 47, and the comparator 48 does not deliver any output signal to the line 49. Accordingly, the electrovalve 35 is not controlled and remains closed. Consequently the compressed air arriving through the bore 20 is unable to escape and continues to act on the lower end of the bar, keeping it in contact with the abrasive surface. When the vibration frequency reaches or exceeds the desired value, the output signal of the comparator 48 is no longer zero and controls the opening of the electrovalve 35. The opening of this electrovalve connects the exhaust bore 36 to the atmosphere. This results in a significant reduction in the force acting on the lower end of the bar, because the air under pressure is now able to escape, on the one hand through the lateral nozzle 10, the lateral cavity 21 and the bore 17, and on the other hand through the central cavity 11, the bore 15 and the bore 16. The bar 1 thus moves into a lower position in which it is no longer in contact with the abrasive surface.

In one variant (not shown), the two-level pneumatic force enabling the bar to be kept in an upper position or a lower position, may be obtained by controlling the electrical inlet valve 30 by means of the output signal of the comparator 9, so that it applies a pressure keeping the bar in its upper position in the absence of a signal at the output of the comparator, and eliminating said pressure on the appearance of a signal at the output of the comparator, so that the bar moves into its lower position, exhaust optionally taking place at atmospheric pressure.

Accordingly, the present invention offers a simple means of measuring the vibration frequency of a metal bar. In addition, in cases where the frequency measured is not the desired frequency, the invention provides for simple automatic adjustment of the width of the bar to obtain the desired vibration frequency.

The vibration frequency of the bar corresponds better to the desired value, the narrower the bandwidth of the selective amplifier. In addition, a narrow bandwidth makes it possible to prevent the interference in the response of the amplifier of the vibration frequencies of other possible modes of vibration at frequencies which are multiples of the central frequency of the amplified band. A good signal-to-noise ratio, of the order of 10, which is sufficient in practice is obtained in this way.

Referring to one purely illustrative Example, the ferromagnetic bar is in the form of a cylinder with a diameter of 4.5 mm and a length of 19 mm. The pressure of the compressed air source is equal to 2 bars and exhaust takes place at atmospheric pressure. The interval between the lower end of the insulating tube and the upper surface of the distribution block is of the order of 1 mm. On the other hand, the clearance between the bar and the insulating tube is of the order of 5/100 mm. This clearance may be larger if desired, although it should not exceed 0.2 mm.

The rotational speed of the support of the grinder and the diameter thereof should be adjusted in such a way that the speed of the grinder at the level of the bar amounts to between 1 m/s and 25 m/s and preferably to 23 m/s.

The 3 db bandwidth of the selective amplifier is governed by the precision required for frequency adjustment and preferably corresponds to 0.01 % of the value of the desired frequency.

Finally, it is possible by virtue of the invention to detect any vibration frequency by regulating the central frequency of the bandwidth of the selective amplifier, and to adjust the length of the bar accordingly.

We claim:

1. An apparatus for measuring the natural vibration frequency of a ferromagnetic metal bar comprising
a vertical insulating cylinder (2);
pneumatic means to freely suspend the bar at the center of the cylinder (2) including
a compressed air source (6) of constant adjustable output in pressure,
a distribution block (5) connected to the lower part of the insulating cylinder (2),
a connecting element (7) formed with an inner cavity (8),
a central air inlet nozzle (9) connected to the compressed air source, the lower end of the insulating cylinder (2) and the upper end of the central air inlet nozzle (9) opening directly into the cavity, the cavity (8) being situated in the extension of the insulating cylinder (2) and connected to the compressed air source by said central nozzle,
and at least one lateral exhaust nozzle (10, 50) in pneumatic communication with cavity (8) the pressure within the cavity defining the equilibrium position of the bar;
vibration application means (53, 54, 55; 57, 58; 3, 4) acting on the bar (1) to cause the bar to vibrate;
a solenoid (40) which establishes a constant magnetic field, the terminals (41, 42) of the solenoid having the vibration frequency of the bar superimposed thereon for the detection thereof;
and a selective amplifier (43, 44) connected to the terminals (41, 42) of the solenoid (40).

2. Apparatus as claimed in claim 1, wherein the cavity (8) formed in the connecting element (7) is circular.

3. Apparatus as claimed in claim 1 further comprising frequency measuring means (56) connected to the terminals of the selected amplifier to directly measure the vibration frequency of the bar (1).

4. An apparatus as claimed in claim 3, wherein the frequency-measuring means is a frequency-meter.

5. An apparatus as claimed in claim 3, wherein the frequency-measuring means is a chronometer which measures the time necessary for counting a predetermined number of passages through zero of the signal appearing at the terminals of the first solenoid.

6. An apparatus as claimed in claim 1, wherein the means causing the bar to vibrate are in the form of a hammer (53) which strikes the upper end of the bar (1), and wherein the central nozzle comprises means (52) for limiting the downward stroke of the bar under the action of the hammer.

7. An apparatus as claimed in claim 6, wherein said stroke-limiting means are in the form of an elbow bend in the central nozzle, and an elastic stop (52) located at the base of the nozzle at the bend thereof.

8. An apparatus as in claim 1, wherein the means causing the bar to vibrate are a second solenoid (57) surrounding the first solenoid,
and a pulse generator (58) which delivers an extremely brief impulse of high intensity connected to the second solenoid.

9. Apparatus as claimed in claim 1 and additionally comprising means to modify the bar and hence modifying its vibration frequency to bring it to the desired value, wherein
the means causing the bar to vibrate are an abrasive tool (3, 4);
a comparator (48) is provided, connected to the selective amplifier (43, 44) and comparing the measured value of the frequency with a signal representing said desired value,
the output signal of the comparator controlling the interaction between the tool and the end of the bar by, selectively, controlling the supply of compressed air to, or from said cavity (8).

10. Apparatus as claimed in claim 9, wherein said abrasive tool (3, 4) comprises a grinding wheel rotating in a horizontal plane and arranged near the upper end of the vertical insulating cylinder (2).

11. Apparatus as claimed in claim 9, further comprising controlled valve means (35), connected and controlled by the output from said comparator (48) having pneumatic communication with said cavity (8).

12. Apparatus as claimed in claim 9, wherein the distribution block (5) is formed with a central cavity (11);
the lower end of the central nozzle (9) opens into the central cavity;
a first lateral cavity (13) connected to the compressed air source (6) and in pneumatic communication with said central cavity (11) compressed air flow regulating means (18) controlling the flow of compressed air from said source to said first lateral cavity (13);

a second lateral cavity (21) formed in the distribution block (5) and in pneumatic communication with the lateral nozzle (10) and with the exhaust from said apparatus;

and a flow regulating means (22) between said second lateral cavity (21) and the exhaust.

13. An apparatus as claimed in claim 12, wherein the flow-regulating means are in the form of point screws.

14. An apparatus as claimed in claim 9, wherein the solenoid (40) is mounted on the lower part of the insulating cylinder (2) in a position corresponding to the upper position of the bar, and wherein the lateral nozzle (10, 40) opens in a position which defines the lower position of the bar.

* * * * *

UNITED STATES PATENT AND TRADEMARK OFFICE
CERTIFICATE OF CORRECTION

PATENT NO. : 4,012,870
DATED : March 22, 1977
INVENTOR(S) : Michel G. BERNIERE et al.

It is certified that error appears in the above–identified patent and that said Letters Patent are hereby corrected as shown below:

Please list the assignee as follows:

SOCIETE ANONYME DE TELECOMMUNICATIONS
    PARIS, FRANCE a corporation of France

Change title to read: "APPARATUS FOR MEASURING AND CHANGING VIBRATION FREQUENCY OF METAL BAR"

Signed and Sealed this

Twenty-eighth Day of June 1977

[SEAL]

Attest:

RUTH C. MASON
*Attesting Officer*

C. MARSHALL DANN
*Commissioner of Patents and Trademarks*